(12) United States Patent
Gekeler et al.

(10) Patent No.: US 9,199,080 B2
(45) Date of Patent: Dec. 1, 2015

(54) METHOD FOR TREATING AN EYE

(75) Inventors: Florian Gekeler, Tuebingen (DE);
Walter G. Wrobel, Reutlingen (DE);
Andre Messias, Ribeirao Preto (BR)

(73) Assignee: Okuvision GmbH, Reutlingen (DE)

( * ) Notice: Subject to any disclaimer, the term of this patent is extended or adjusted under 35 U.S.C. 154(b) by 281 days.

(21) Appl. No.: 13/199,904

(22) Filed: Sep. 12, 2011

(65) Prior Publication Data

US 2013/0066396 A1    Mar. 14, 2013

(51) Int. Cl.
*A61N 1/36* (2006.01)
*A61N 1/04* (2006.01)

(52) U.S. Cl.
CPC .......... *A61N 1/36046* (2013.01); *A61N 1/0456* (2013.01); *A61N 1/36014* (2013.01)

(58) Field of Classification Search
USPC ...................................... 607/53–54
See application file for complete search history.

(56) References Cited

U.S. PATENT DOCUMENTS

| | | | |
|---|---|---|---|
| 4,417,581 A * | 11/1983 | Dawson | ........................ 600/383 |
| 5,836,996 A | 11/1998 | Doorish | |
| 6,032,062 A | 2/2000 | Nisch | |
| 6,275,735 B1 | 8/2001 | Jarding et al. | |
| 6,315,940 B1 | 11/2001 | Nisch | |
| 6,458,157 B1 | 10/2002 | Suaning | |
| 7,321,795 B2 | 1/2008 | Bogdanowicz | |
| 8,457,752 B2 * | 6/2013 | Greenberg et al. | ............. 607/54 |
| 2002/0150933 A1 | 10/2002 | Ehricht et al. | |
| 2003/0068613 A1 | 4/2003 | Leibrock et al. | |
| 2004/0176820 A1 | 9/2004 | Paul | |
| 2005/0064469 A1 | 3/2005 | Schulz et al. | |
| 2006/0078929 A1 | 4/2006 | Bickel et al. | |
| 2006/0184214 A1 | 8/2006 | McDaniel | |
| 2006/0184245 A1 | 8/2006 | Graf et al. | |
| 2007/0053996 A1 | 3/2007 | Boyden et al. | |
| 2007/0123766 A1 | 5/2007 | Whalen, III et al. | |
| 2008/0288021 A1 * | 11/2008 | Schmid | ........................ 607/54 |
| 2009/0011536 A1 | 1/2009 | Zhang et al. | |
| 2009/0192571 A1 | 7/2009 | Stett et al. | |
| 2009/0222062 A1 | 9/2009 | Rothermel | |

FOREIGN PATENT DOCUMENTS

| | | |
|---|---|---|
| DE | 195 29 371 | 2/1997 |
| DE | 197 12 309 | 3/1997 |
| DE | 102 01 463 | 7/2003 |
| DE | 103 15 074 | 10/2004 |
| DE | 10 2006 048 819 | 4/2008 |
| EP | 0 460 320 | 8/1990 |
| WO | WO-01/02094 | 1/2001 |

(Continued)

OTHER PUBLICATIONS

Examination Report for DE 10 2009 061 008.1, issued Oct. 22, 2013, 7 pages.

(Continued)

*Primary Examiner* — Paula J Stice
(74) *Attorney, Agent, or Firm* — Morrison & Foerster LLP

(57) ABSTRACT

In a method for treating at least one eye of a patient in need of such treatment with a pulsed electrical stimulation signal, first an individual parameter of the patient is determined, thereafter at least one stimulation parameter of the pulsed electrical stimulation signal is set depending on the at least one individual parameter, and then the pulsed electrical stimulation signal is applied to the at least one eye.

23 Claims, 4 Drawing Sheets

(56) References Cited

FOREIGN PATENT DOCUMENTS

| WO | WO-01/65251 | 9/2001 |
|---|---|---|
| WO | WO-2004/067088 | 8/2004 |
| WO | WO-2004/067734 | 8/2004 |
| WO | WO-2005/000395 | 1/2005 |
| WO | WO-2007/121901 | 11/2007 |
| WO | WO-2007/128404 | 11/2007 |
| WO | WO-2008/037362 | 4/2008 |
| WO | WO-2008/089003 | 7/2008 |
| WO | WO-2010/105728 | 9/2010 |
| WO | WO-2011/086150 | 7/2011 |

OTHER PUBLICATIONS

Chow et al., "The Artificial Silicon Retina Microchip for the Treatment of Vision Loss from Retinitis Pigmentosa," Archives of Opthalmology (2004) 122:460-469.

Dawson et al., "Improved Electrode for Electroretinography," Investigative Opthalmolmology & Visual Science (1979) 18(9) 988-991.

Fujikado et al., "Effect of Transcorneal Electrical Stimulation in Patients with Nonarteritic Ischemic Optic Neuropathy or Traumatic Optic Neuropathy," Japanese Journal of Opthalmology (2006).

Gall et al., "Noninvasive Transorbital Alternating Current Stimulation Improves Subjective Visual Functioning and Vision-Related Quality of Life in Optic Neuropathy," Brain Stimulation (2011) 4:175-188.

Gekeler et al., "Phosphenes Electrically Evoked with DTL Electrodes: A Study in Patients with Retinitis Pigmentosa, Glaucoma, and Homonymous Visual Field Loss and Normal Subjects," Investigative Opthalmology & Visual Science (2006) 47(11) 4966-4974.

Schatz et al., "Transcorneal Electrical Stimulation for Patients with Retinitis Pigmentosa—a Prospective, Randomized, Sham-Controlled Exploratory Study," Investigative Opthalmology & Visual Science (published online Apr. 5, 2011) Manuscript iovs 10-6932.

International Preliminary Report on Patentability for International Application No. PCT/EP2010/001126, issued Sep. 20, 2011, 12 pages.

International Search Report for International Application No. PCT/EP2010/01126, issued Sep. 20, 2010, 17 pages.

Lagali et al., "Light-Activated Channels Targeted to ON Bipolar Cells Restore Visual Function in Retinal Degeneration," Nat. Neurosci. (2008) 11(6):667-675.

Vogel et al., "Optoelektronische Bauelemente mit Integriertem Lichtemitter," Elektronik (2009):54-58 (with English summary abstract).

International Preliminary Report on Patentability and Written Opinion for PCT/EP2012/066411, issued Mar. 12, 2014, 7 pages.

Restriction Requirement issued in U.S. Appl. No. 13/236,569, dated Mar. 28, 2014, 8 pages.

Examination Report for German Patent Application DE 10 2009 015 389.6, issued Aug. 12, 2013, 21 pages.

Response to Examination Report in German Patent Application DE 10 2009 015 389.6, dated Apr. 23, 2014, 12 pages.

Response to Examination Report in German Patent Application DE 10 2009 061 008.1, dated Apr. 22, 2014, 2 pages.

Response to Restriction Requirement for U.S. Appl. No. 13/236,569, filed May 27, 2014, 9 pages.

Office Action for U.S. Appl. No. 13/236,569, mailed Jun. 26, 2014, 9 pages.

Response to Office Action for U.S. Appl. No. 13/236,569, dated Sep. 18, 2014, 15 pages.

Final Office Action for U.S. Appl. No. 13/236,569, issued Feb. 6, 2015, 10 pages.

* cited by examiner

METHOD FOR TREATING AN EYE

BACKGROUND OF THE INVENTION

The present invention relates to a method for treating at least one eye of a patient in need of such treatment.

The method is envisaged for treating one eye of the patient at a time, both eyes concurrently together or one eye after the other.

RELATED PRIOR ART

Retinal diseases are currently the subject of thorough research in ophthalmology.

Whereas drug medication has now already become available for age-related degenerative diseases such as "wet" age-related macular degeneration (AMD), none have yet been approved for those of genetic origin, such as Retinitis Pigmentosa (RP).

This disease is particularly serious in that it often affects persons in the active period of their lives. About one person in every 4,000 person is affected by it, thus making it the most common hereditary eye disease. It reduces the visual field over a course of years, usually starting from the periphery, and results in tunnel vision; in the final stages, visual function often disappears completely.

Although electrical retinal implants for restoring loss vision at least partly have been clinically tested, such systems come into question only when the loss of vision has already progressed very far. During the years before that, however, when the patient knows his diagnosis and must live with the awareness that he will possibly lose his sight completely in future, there is still no generally accepted and scientifically recognized therapeutic option for prevention. Vitamin A doses have not been accepted in standard practice.

This is where electrical stimulation of the retina comes in. The initial impulse for this idea came from basic research with electrical retinal implants in recent years. Such research indicated that electrical stimulation of the retina liberates growth factors which may be able to delay retinal degeneration.

The idea of using electrical current therapeutically is as old as our knowledge of electricity itself. Electric stimulation of the retina, with particular emphasis on implants, has been the subject of intensive research in recent years.

Chow et al., "The artificial silicon retina microchip for the treatment of vision loss from retinitis pigmentosa", in Arch.Ophthalmol. 2004; 122; 460-469, report that patients with a passive subretinal implant were able to discern phosphenes even at retinal locations where the implant was not located.

The assignee of this application has received a personal communication according to which patients equipped with an active subretinal implant reported subjective improvement in their "visual faculty" (e.g. less glare sensitivity etc.) even after explantation of the chip.

This experience suggested that electrical stimulation leads to a release of growth factors which—for the time being, at least—ward off a further advance of retinal degeneration. Earlier studies were apparently unable to demonstrate this due to methodic deficiencies.

In particular, the challenge was to design a system which would hopefully require only a single adjustment by an expert with normal vision and then, after being installed, could give even patients with severely handicapped vision the ability to use the system independently under a physician's supervision in the surroundings of their own homes.

Such a known system involves a thread electrode that is mounted on a device designed like a lens frame or a face mask. When this device is fitted to a patient's facial eye area, the slender thread electrode comes into contact with the corneal surface of the eye. A counter electrode is either provided on the device or is attached to the temple. Via the thread electrode and the counter electrode a pulsed electrical stimulation signal can be applied to the eye, this leading to the flow of a stimulation current via the cornea into the eye.

Such devices are disclosed in WO 2011/086150 A2 of the present assignee. The disclosure of this document is incorporated by reference into the present application.

SUMMARY OF THE INVENTION

After a clinical study of the inventors at the University Eye Hospital of Tübingen showed that the visual field can be improved by means of electrostimulation, and indications of improvement in vision and other parameters were also found, a new concept of therapy was developed.

Namely, said clinical studies of the inventors indicate that stimulation of the retina with small amounts of current can have a therapeutic effect on retinal diseases such as retinitis pigmentosa. The inventors have therefore developed a therapeutic or preventive treatment method which stimulates the eye with a thread electrode.

Pulsed electrical stimulation of the retina above a certain intensity results in the perception of electrically triggered light phenomena, so-called "phosphenes". Studies of patients with retinal degeneration have shown that the threshold differs widely from patient to patient but tends to rise as retinal degeneration progresses; see Gekeler et al., "Phosphenes electrically evoked with DTL electrodes: a study in patients with retinitis pigmentosa, glaucoma, and homonymous visual field loss and normal subjects", in Investigative Ophthalmology & Visual Science 2006; 47; 4966-4974.

In some embodiments, this observation led the inventors to the idea of electrical stimulation with a percentage, e.g. a fixed percentage of individual threshold values, thus ensuring that stimulation could be administered with equal intensity to every patient in the groups compared.

In view of this background, the inventors have found that a positive effect of electrical stimulation is to be expected only when the stimulation does in fact lead to a release of phosphenes. Studies to date have not taken this individuality of the patients into account.

To the contrary, U.S. Pat. No. 6,275,735 B1 explicitly teaches to treat the eye of a person suffering from macular degeneration by providing a microcurrent between about 50 to about 350 microampere through four points on the upper eyelid and four points on the lower eyelid, whereby the level of the current is selected such that the patient just does not see light flashes. Light flashes are nothing else than phosphenes.

The known method suggests that the current applied to the eyelid is brought up until the patient sees light flashes and/or feels the tinge of electricity. The current is then decreased so that the patient feels no discomfort. This is the preferred current level used for therapy according to this piece of prior art.

The preferred current level according to the known method is between about 150 to about 250 microampere.

According to one object, the present invention relates to a method for treating at least one eye of a patient in need of such treatment, comprising the step of applying a pulsed electrical stimulation signal to the at least one eye, wherein at least one stimulation parameter of the pulsed electrical stimulation signal is set depending on at least one individual parameter of the patient.

It is another object to provide a method for treating at least one eye of a patient in need of such treatment, the method comprising the step of applying a pulsed electrical stimulation signal to the at least one eye, such that the pulsed electrical stimulation signal stimulates the at least one eye with a stimulation current that is higher than a base line stimulation current that corresponds to an individual phosphene threshold of the at least one eye of that patient.

The at least one stimulation parameter may be selected at the beginning of each treatment, either by the patient or a third person, or may be determined once, stored in appropriate manner, and then be used for all treatments.

According a further object, there is provided a method for treating at least one eye of a patient in need of such treatment with a pulsed electrical stimulation signal, wherein first an individual parameter of the patient is determined, thereafter at least one stimulation parameter of the pulsed electrical stimulation signal is set depending on the at least one individual parameter, and then the pulsed electrical stimulation signal is applied to the at least one eye.

In the meaning of the present invention, "a patient in need of such treatment" is generally understood to be a person that suffers from certain eyes diseases or conditions, especially from Retinitis Pigmentosa (RP), or has a genetic disposition for such eye diseases, or just feels to be in need for such treatment. Such eye diseases and conditions may further but not exclusively include Macular detachment, Glaucoma, Macular Degeneration, Retinal Detachment, Retinal Artery Occlusion, Retinal Vein Occlusion, Non-Arteriitic Anterior Ischemic Optic Neuropathy, Ischemic Macula Edema.

According to one object, the at least one stimulation parameter is a stimulation current flowing via the cornea into the at least one eye.

It is a further object that the at least one individual parameter is a base line stimulation current that is just sufficiently high enough to result in the perception of electrically triggered light phenomena in the at least one eye of that patient.

According to still another object, the at least one eye is stimulated with a stimulation current that is higher than the base line stimulation current. The stimulation current is preferably at least 110% of the base line stimulation current, is preferably between 110% and 200%, more preferably between 140% and 160% of the base line stimulation current.

According to a further object, the base line stimulation current is determined individually for each patient by applying to the at least one eye a pulsed electrical stimulation signal which has initially a stimulation current low enough as to not elicit a phosphene, increasing the stimulation current until the patient reports the perception of a phosphene, taking the corresponding stimulation current as the instant base line stimulation current, and setting the at least one stimulation parameter depending on the instant base line current.

The stimulation current can be increased linearly in increments or in logarithmic fashion, e.g. by 30% in each new round, whereby in a first round larger increments or percentages may be used to determine a rough estimate for the base line stimulation current. In the next round the stimulation current is chosen to be below the estimate for the base line stimulation current, and is then increased in smaller increments or percentages until a new estimate for the base line stimulation current is determined. This procedure may be repeated several times.

In an improvement, it is preferred if the instant base line stimulation current is determined at least three times in succession and the arithmetic mean value of said three instant base line stimulation currents is calculated and used as the instant base line stimulation current for subsequent treatments of the at least one eye.

This has the advantage that the stimulation current used for treatment is determined based on the individual phosophene threshold of the respective patient.

In the meaning of the present invention, "an individual phosophene threshold" is understood to mean a stimulation current that is just sufficiently high enough to result in the perception of electrically triggered light phenomena, the so-called phosphenes. If the stimulation current is equal or higher than this base line stimulation current, phosphenes are elicited. If the stimulation current has a strength below this base line, in the specific patient no phosphene are elicited. However, as the base line is an individual value, a stimulation current of this strength may evoke a phosphene in another patient.

The pulsed electrical stimulation signal may comprise a succession of current pulses and has a stimulation duration time, a pulse duration time and a pulse repetition frequency.

According to one object, the pulsed electrical stimulation signal comprises a stimulation duration time of about 30 min, a succession of biphasic current pulses having each a pulse duration time of about 5 ms positive directly followed by 5 ms negative pulse, and a pulse repetition frequency of about 20 Hz.

The treatment may be repeated once per week and this again and again for many months or even years.

The method may comprise the step of attaching a thread electrode to the at least one eye, such that it makes direct or indirect electrical contact to the cornea, and a counter electrode to a skin portion of the patient, the thread electrode and the counter electrode being part of an electrical circuit for applying the pulsed electric stimulation signal to the at least one eye; the counter electrode may be attached to the temple; the thread electrode may positioned in the conjunctival sac or on the edge of the lid of the at least one eye.

The thread electrode may be fixed in place on the face of the patient by appropriate means like adhesive skin plasters. The thread electrode may alternatively be positioned in place by using the lens frame or the face mask as disclosed in WO 2011/086150 A2 mentioned above.

The treatment can be performed at home by the patient, once the individual parameters have been determined by a qualified person. However, it is also envisaged that the method may be performed at a doctor's practice or a health center or a specialized service center.

At these centers or practices the phosphene threshold is determined either at a first visit of the patient, and the so determined instant base line stimulation current is used for all further treatment sessions, which may be done at home or at other facilities. However, it is also envisaged that at the beginning of each treatment session the qualified person determines the individual phosphene threshold anew, so that each treatment takes into account a possible shift of the individual phosphene threshold, what shift may be the result of the previous treatment sessions.

In this connection, it is envisaged that the pulsed electric stimulation signal is generated by a control unit which has stored therein variable parameters for said pulsed electric stimulation signal, said parameters comprising at least a value representing the stimulation current. The stimulation current value is determined by a qualified person different from the patient, and stored into the control unit such that it can be altered only by any qualified person. To this end, the qualified person determines the instant base line stimulation current as described above, and then sets the value for the stimulation current depending on the instant base line stimulation current.

This ensures that the patient can not alter the parameters of the treatment, either deliberately or unintentionally.

The stimulation current value may be stored on a data memory that can be put into communication with the control unit.

By this, only the qualified person can store and alter the parameters. The data carrier can be a memory stick that is plugged into the control unit, or may be a computer that communicates with the control unit via internet or other wired or wireless communication channels.

The inventors have conducted and published the clinical study proving the above findings and objects; see Schatz et.al., "Transcorneal Electrical Stimulation for Patients with Retinitis Pigmentosa—a Prospective, Randomized, Sham-Controlled Exploratory Study", in Investigative Ophthalmology & Visual Science, (in press, published online on Apr. 5, 2011, as manuscript iovs.10-6932).

The disclosure of that publication is incorporated into this application by reference.

A further object of the invention is a method for determining at least one stimulation parameter of a pulsed electrical stimulation signal to be used for treating at least one eye of a patient in need of such treatment, comprising the step of selecting said at least one stimulation parameter of the pulsed electrical stimulation signal depending on at least one individual parameter of the patient.

According to one object, the at least one individual parameter is a base line stimulation current that is just sufficiently high enough to result in the perception of electrically triggered light phenomena in the at least one eye of that patient, and wherein the at least one stimulation parameter is a stimulation current that is higher than an instant base line stimulation current, the base line stimulation current being determined individually for each patient by applying to the at least one eye a pulsed electrical stimulation signal which has initially a stimulation current low enough as to not elicit a phosphene, increasing the stimulation current until the patient reports the perception of a phosphene, taking the corresponding stimulation current as the instant base line stimulation current, and setting the at least one stimulation parameter depending on the instant base line current.

In view of the above, the present invention also provides a system for treating at least one eye of a patient in need of such treatment, comprising a means of applying a pulsed electrical stimulation signal to the at least one eye; and a control unit which has stored therein variable parameters to generate the pulsed electrical stimulation signal based on at least one individual parameter of the patient.

According to one object, the means of applying a pulsed electrical stimulation signal to the at least one eye comprises a thread electrode that can be electrically connected directly or indirectly to the cornea of a patient, and a counter electrode that can be attached to a skin portion of the patient, the thread electrode and the counter electrode being part of an electrical circuit for applying the pulsed electric stimulation signal to the at least one eye, wherein the variable parameters preferably comprise at least a value representing the stimulation current.

According to a further object, the system comprises means that allows determination, storage into the control unit and subsequent alteration of the stimulation current value only by a qualified person, wherein the qualified person preferably is not the patient.

DESCRIPTION OF PREFERRED EMBODIMENTS

The Clinical Study

Figure 1:
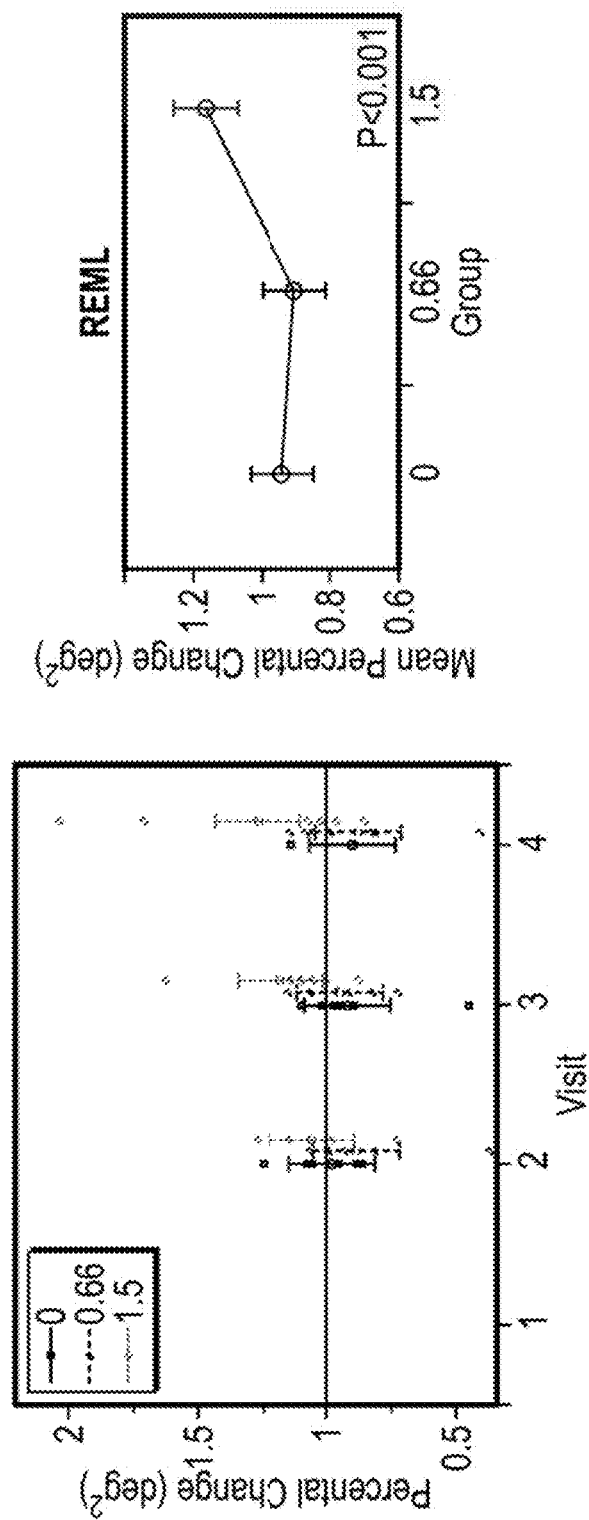
FIG. 1 shows the development of the visual field area in kinetic perimetry for the different treatment arms.

A Clinical Study was performed to assess the safety of transcorneal electrical stimulation (TES) and explore its efficacy in various subjective and objective parameters of visual function in patients with retinitis pigmentosa (RP); see Schatz et al., loc. cit.

Twenty-four patients in this prospective, randomized, partially-blinded, good-clinical-practice conform study received TES (5 ms biphasic pulses; 20 Hz; DTL (Dawson-Trick-Litzkow) electrodes) 30 minutes per week for 6 consecutive weeks. Patients were randomly assigned to one of three groups: sham, 66%, or 150% of individual electrical phosphene threshold (EPT). Visual acuity (VA), visual field (VF; kinetic, static), electroretinography (Ganzfeld, multifocal), dark-adaptation, color discrimination, and EPTs were assessed at all visits or 4 times according to the study plan.

After determination of the individual phosphene threshold in each case, the patients were randomized and divided into the 3 groups. The first (sham) group was treated without electric current, the second with 66% of the individual phosphene threshold (the base line stimulation current), the third with 150%.

TES using DTL (Dawson-Trick-Lizkow) electrodes was tolerated well; all patients concluded the study. Two adverse (foreign body sensation) but no serious adverse events were encountered. There was a tendency for most functional parameters to improve (8/18) or remain constant (8/18) in the 150% group; VF area and scotopic b-wave-amplitude reached statistical significance (P<0.027 and <0.001, respectively). Only desaturated colour discrimination and VF mean sensitivity decreased (the latter due to the enlargement of VF area). There was no obvious trend in the 66% group.

Twenty-four eyes of said 24 patients were included; all suffered from advanced RP (rod-cone-dystrophy). Diagnosis was established by detailed history, funduscopy, electroretinography (ERG), and visual field (VF) examination. Inclusion criteria were age >18 years, visual acuity (VA) 0.02-0.9 (Snellen) and recordable ERG and VF results. Exclusion criteria were other ocular diseases (advanced diabetic retinopathy, retinal or choroidal neovascularization, exudative age-related macular degeneration), silicon oil tamponade, and severe general disease.

Patients were recruited from the hospital's special retinal degeneration clinic. After inclusion they were randomized to one of the three treatment arms: sham stimulation, stimulation with 66% of their individual electrical phosphene threshold (EPT) at 20 Hz, or with 150% of their individual EPT. Mean age was 55.63±14.79 (±SD), 51.63±8.02, and 56.38±13.39 in the sham, 66%, and 150% group, respectively (resp.); there was no statistically significant difference between groups (P=0.72; ANOVA).

Patients and technicians who performed ERG, multifocal ERG (mfERG), VF, darkadaptation (DA) and color discrimination tests were blinded for their treatment group for the entire study period. The examining doctor who performed VA, EPT, intra-ocular pressure (IOP), and slit-lamp examination was not blinded because he/she was responsible for setting of stimulation parameters. The study was approved by the local ethics committee and local agencies; and was registered at clinicaltrials.gov (NCT00804102). All patients gave written informed consent after explanation of the nature and possible consequences of the study; all procedures adhered to the Declaration of Helsinki.

Patients were seen at 9 visits: for one baseline visit (visit 1), followed by 6 consecutive weekly visits (visits 2-7) with TES (dates varied max. ±2 days), and for 2 follow-up visits (visit 8 and 9), one 2 weeks and one 11 weeks after the last stimulation visit (the last dates varied max. ±10 days). Visits 2, 3, 4, 6, 7 were 'short' visits which included: VA, slit lamp biomicroscopy, and TES. Visits 1, 5, 8, 9 were 'long' visits and additionally included: VF, color test, dark-adaptation (DA), ERG and mfERG, optical coherence tomography (OCT). To adjust for learning effects in VF examinations this test was performed at visit 1 and visit 2.

For electrical stimulation a sterile single-use DTL electrode (Diagnosys UK Ltd, Cambridge, UK) was used as active electrode as described in the original publication of Dawson et al., "Improved electrode for electroretinography", in Invest Ophthalmol VisSci, 1979; 18: 988-991.

On the patient's request a local anesthetic was applied to the lower fornix (e.g. oxybuprocaine hydrochloride). A gold cup electrode (LKC Technologies, Inc., Gaithersburg, Md., USA) as counter electrode was attached to the ipsilateral temple after thorough cleaning of the skin and application of contact paste. For stimulation a commercially available neurostimulator was adapted by the manufacturer to deliver current pulses within the range of the study (Twister®, Dr. Langer Medical, Waldkirch, Germany). Rectangular biphasic current pulses (5 ms positive directly followed by 5 ms negative) were applied for 30 minutes at a frequency of 20 Hz. Room light was switched on during the entire session. For sham stimulation all electrodes and cables were attached and EPTs were determined, but stimulation was not turned on.

To assess EPTs an alternative forced choice method was used as described by Gekeler et al., loc. cit. The threshold was determined three times and the average was formed at each study visit for calculation of individual stimulation strength according to the treatment arm.

Ganzfeld ERGs were registered according to the ISCEV standard (International Society for Clinical Electrophysiology of Vision) using a ColorDome® controlled by an Espion $E^2$® (Diagnosys LLC, Cambridge, UK). After 30 minutes of dark adaptation and application of two drops of tropicamide 0.5% (Mydriatikum Stulln®, Stulln, Germany) self constructed DTL-electrodes and gold-cup electrodes (VIASYS Healthcare, Warwick, UK) were positioned on the forehead and the temples. The ERG protocol consisted of 4 steps with intensities from 0.1 to 3 phot cd*s/m$^2$ and 4 ms duration (white 6500 K). Two single flash responses were used as rod protocol and a single-flash response (3 phot cd*s/m$^2$ with a background illumination of 30 phot cd/m$^2$=standard flash, SF) and a 30 Hz flicker were chosen as cone protocol. Impedance level was <10 kΩ. A band-pass filter was applied from 0.3 to 300 Hz using the machine's built-in software algorithm. ERG potentials <5 µV were excluded from the analysis.

Multifocal ERGs were recorded with a Veris™ (Electro-Diagnostic Imaging Inc., Redwood City, USA; software version Veris Science™ 4.9.1) system using a 21 inch screen (resolution 1024×768; "UHR21L", Nortech Imaging Technologies, Plymouth, USA) positioned 32 cm in front of the subject. The visual field stimulated subtended an area of 60°×55°; 61 hexagons were presented with alternating black (5 cd/m$^2$) and white (100 cd/m$^2$) fields. The built-in software algorithm allowed recordings between 10 and 100 Hz (band-pass filter), amplified by a factor of 200,000. Multifocal ERGs (mfERGs) were analyzed by rings, according to the ISCEV guidelines.

An Octopus 900® perimeter (Haag-Streit Inc., Koeniz, Switzerland) was used to conduct VF examinations; background luminance was 10 cd/m$^2$. For semi-automatic kinetic perimetry up to 90° eccentricity white stimuli (Goldmann III4e with a constant angular velocity of 3°/s) were used. Stimuli were presented every 15°. Isopter and scotoma areas (in deg$^2$) were quantified using the built-in software algorithm. As quality criterion for the kinetic perimetry the blind spot was detected with at least 5 stimuli Goldmann size 14e at 2°/s. White-on-white static perimetry was conducted using a fast threshold strategy GATE (German Adaptive Thresholding Estimation) up to 85° eccentricity. A test grid consisting of 86 stimulus locations which were condensed towards the centre was applied (stimulus size: Goldmann III, presentation duration: 200 ms, response time: 1200 ms).

A Stratus OCT® Model 3000 (Carl Zeiss Meditec GmbH, Oberkochen, Germany) scanned in "radial lines" mode; foveal thickness was retrieved after manual verification of the detection borders of the software algorithm, and used for optical coherence tomography.

For ophthalmological examination, Snellen VA was assessed using a projector at a viewing distance of 6 m (SCP-660®, Nidek Inc., Fremont, Calif., USA).

Intra-ocular pressure was tested using Goldmann applanation tonometry (Haag Streit, Bern, Switzerland).

A DARKadaptometer® (Roland Consult Stasche&Finger GmbH, Brandenburg, Germany) was used to determine final thresholds for cones (red test light, 625 nm) and rods (green test light, 530 nm) after 20 minutes of dark-adaptation with maximally dilated pupils.

Color discrimination was tested monocularly using Farnsworth D-15 (saturated) and Lanthony Desaturated D-15 presented under a Judge II Light Testing Box® (Gretag MACBETH, Neu-Isenburg, Germany) at 6500 K. The saturated test was scored using the Color Confusion Index (CCI); the desaturated test using the total error score (TES). Scoring was performed by a web-based software (http://www.torok.info/colorvision/d15.htm).

Examinations at visits 1 and 9 included: general appearance, neck, extremities and joints, skin, lymph nodes, auscultation of lungs and heart, venous blood samples for: complete blood count, electrolytes, and basic renal and hepatic values.—Pulse rate, blood pressure, and body temperature were taken at all visits.

Ten percent of all data extracted from the electronic case report forms (eCRFs) were randomly chosen to be double-checked manually using the monitoring process before statistical analysis was performed using JMP® (version 8.0.1.0; SAS Institute, Inc., Cary, N.C., USA). Descriptive statistics were used to summarize data with illustrations of means and 95% confidence intervals. To analyze the influence of treatment intra-individual differences were calculated for each subject between baseline and follow-up visits. Comparison between treatment groups was performed using the method of restricted maximum likelihood (REML) to estimate the development of parameters under treatment during visits for each group. In contrast to maximum likelihood estimation, REML can produce unbiased estimates of variance parameters. To compare groups Tukey-Kramer post-hoc test analysis was applied with a global level of significance set at p<0.05. Due to the exploratory character of the study no single endpoints were declared and no adjustment for multiple testing was performed.

All 24 patients completed the entire follow-up period. Electrical stimulation via DTL electrodes was tolerated well, as reported by Gekeler et al., loc. cit., even when electrodes where not only used for threshold determination with short current pulses but continuously for 30 minutes with suprathreshold currents.

Base line stimulation current values of groups did not differ significantly, with the exception of cone threshold sensitivity (P=0.031). Stimulation current was 0.23±0.13 mA and 0.36±0.18 mA in the 66% and 150% group, resp. (overall mean ±SD).

One patient reported mild foreign body sensation and showed minor irritation of the conjunctiva after IOP measurement, which we related to the anesthetizing drops. Another patient experienced foreign body sensation once after stimulation, which resolved after prescription of artificial tears 2 hourly for one day. No other adverse events or serious adverse events (SAEs) were encountered.

General examinations and blood tests were all within normal ranges at all visits.

During study visits, the dark-adapted a-wave amplitude, elicited by an ISCEV SF, (International Society for Clinical Electrophysiology of Vision Standard Flash),changed by 6.72 µV, −0.07 µV, and 0.64 µV in 150%, 66%, and sham group, resp. (mean REML; P=0.49). The b-wave amplitude changed by 8.79 µV, −8.82, and −8.43 µV in the 150%, 66%, and sham group, resp.; the 150% group differed significantly (P=0.027). No obvious change occurred for implicit times (P=0.90 and 0.96 for a- and b-wave, resp.).

In the photopic ERG the a-wave amplitude changed 1.11 µV, −10.35, and 2.77 µV in the 150%, 66%, and sham group resp.; the incoherent behavior missed statistical significance (P=0.062). The b-wave amplitude changed by 6.66 µV, −0.31 µV, and −0.21 µV in the 150%, 66%, and sham group, resp. (P=0.082). No obvious change occurred for implicit times (P=0.80 and 0.25 for a- and b-wave, resp.).

Snellen VA (in logMAR) changed 0.017, 0.039, and 0.067 in the 150%, 66%, and sham group, resp.; the changed missed statistical significance (P=0.22).

Visual field area changed by 17%, −9%, and −6% in the 150%, 66%, and sham group, resp. (P<0.001). Mean sensitivity in the VF changed by −0.18 dB, −0-09 dB, and 0.66 dB in the 150%, 66%, and sham group, resp. (P=0.12).

The final threshold of rod sensitivity decreased by 0.39 cd/m2, 0.081 cd/m2, and 0.043 cd/m$^2$ in the 150%, 66%, and the sham group, resp. (P=0.53). The final threshold of cone sensitivity decreased by 0.19 cd/m$^2$, −0.019 cd/m$^2$, and −0.084 cd/m2 in the 150%, 66%, and the sham group, resp. (P=0.46).

Sensitivity of electrically evoked phosphenes at 20 Hz increased by 43%, 25%, and 27% in the 150%, 66%, and sham group, resp. (P=0.73).

The CCI of the Farnsworth D-15 saturated changed by 0.058, −0.04, and −0.24 in the 150%, 66%, and sham group, resp.; values changed significantly (P=0.034). The TES of the Lanthony desaturated D-15 changed by 27.99, 2.98, and 14 in the 150%, 66%, and sham group, resp.; values did not change significantly (P=0.72).

To summarize, the inventors found a tendency of improvement in the following 8 examinations after TES: scotopic a- and b-wave amplitudes of the ERG, the photopic b-wave amplitude, Snellen VA, VF area, sensitivity for electrical phosphenes, and cone and rod threshold sensitivity. Some of these changes were small or did not reach statistical significance.

Final evaluation showed an improvement in vision of about +0.05 logMAR in both the sham and 66%-group, but an improvement of about +0.1 logMAR in the 150% group. This means that about one line more can be read on a vision testing chart.

Study of the visual fields showed no change in the sham and 66% groups, but a statistically highly significant improvement (P<0.001) of about +20% in the 150% group; see FIG. 1.

The visual field is to be regarded as particularly critical in importance for patient mobility, since it permits the patient at least to orient himself/herself independently both indoors and outdoors.

The decision to use individual phosphene thresholds in this study instead of fixed predefined amplitudes in each group was based on several thoughts. First, the inventors believed that the stimulation strength which is necessary to produce an effect is dependent on the stage of the disease, i.e. more heavily degenerated retina should require higher current amplitudes. And since EPT is a measure of the disease stage it can be taken as an indicator for stimulation strength. Second, the inventors see a potential beneficial effect of stimulating supra-threshold since this ensures activation of remaining retinal cells, especially ganglion cells and also the whole visual system, an effect which would go beyond stimulation of e.g. Müller cells to enhance production of neurotrophic factors.

Transcomeal electrical stimulation can have several potential advantages over other treatments. First, TES is little invasive and bears almost no danger of adverse or even serious adverse reactions, such as endophthalmitis after intraocular injections or very severe AEs e.g. as gene therapy. Second, EST is cheap, costs of electrodes are low and a stimulator can be built using standard electronic components. Furthermore, parameters of TES can be easily adjusted and there are possibilities to evaluate stimulation parameters after treatment periods through storage of impedance and other parameters in the stimulator unit. Transcomeal electrical stimulation can also stimulate all ocular structures, including the retina, choroid, ciliary body, ganglion cells and optic nerve. On the hypothesis that TES exerts its effect—even if only partially—through activation of any these structures and their respective neurotrophic factors and pathways it could be beneficial to simultaneously affect the expression of a variety of these factors.

Design of an Improved Treatment System

The clinical study was carried out with standard commercial devices of types which have already been in use for years in electrophysiological eye examinations.

Determination of the individual phosphene threshold and the treatment parameters must be carried out by a physician. Since the therapy may last for years, even blind persons should be able to apply the therapy themselves under the direction of a physician.

The Electrode Design

Figure 2:
FIG. 2 shows a photograph of a female patient having a DTL electrode placed on the eye.

The aim is that the patient should be able to administer the treatment in home surroundings. This makes local application of corneal anesthetics in particular impossible, since the risk of injury to visually handicapped patients would be increased by a suppression of the sense of pain. Of all types of eye electrodes, DTL electrodes appear to be best tolerated by the patients; see Gekeler et la., loc. cit. This means that a slender electrically conducting thread is positioned in the conjunctival sac or on the edge of the lid and fixed in place on the face with adhesive skin plasters; see FIG. 2.

The Electrode Holder

However, fixation of DTL electrodes on the face involves problems. The slender fiber is difficult even for staff assistants to recognize, and its fixation on the skin is time-consuming, unreliable, and requires manual dexterity. Prefabricated, disposable electrodes would be a solution for blind persons provided that reproducible positioning on the face would be feasible, with the proviso that only tactile sensation would be present. It must also be possible to check the correctness of electrode positioning on the eye by means of functions built into the stimulation device, since there is no way to ensure that the thread will always be felt.

The Power Supply

With regard to operation of the unit by persons with severe visual handicaps, the electrical current supply should require a minimum of supervision in operation and should also not require an ability to read display devices and the like; rather, any required warning signals and operating instructions should be purely acoustical.

Only the attending physician should be allowed to determine treatment parameters. It is desirable that the physician should have access a posteriori to a treatment protocol showing the time and actual duration of treatment, since experience has shown that patient compliance is often difficult to assess.

The Electrodes

DTL electrodes consist of a plastic thread coated with an inert metal. Depending on thickness, the thread is well tolerated. Very thin filaments are not felt at all, but are also nearly invisible for staff assistants during the positioning process. Thicker filaments which are easier to see are also a source of constant irritation. An empirical compromise must therefore be found.

Additional inquiries were made of several patients concerning their experiences, and electrodes of various thicknesses which had also been tolerance-tested by the investigators on themselves were presented to them. The threads which were selected (monofilament, 0.1 mm in diameter) lie securely on the corneal surface or the edge of the lid and engender only the same kind of irritation as that created by an eyelash, for example. Local anesthesia is unnecessary.

Figure 3:
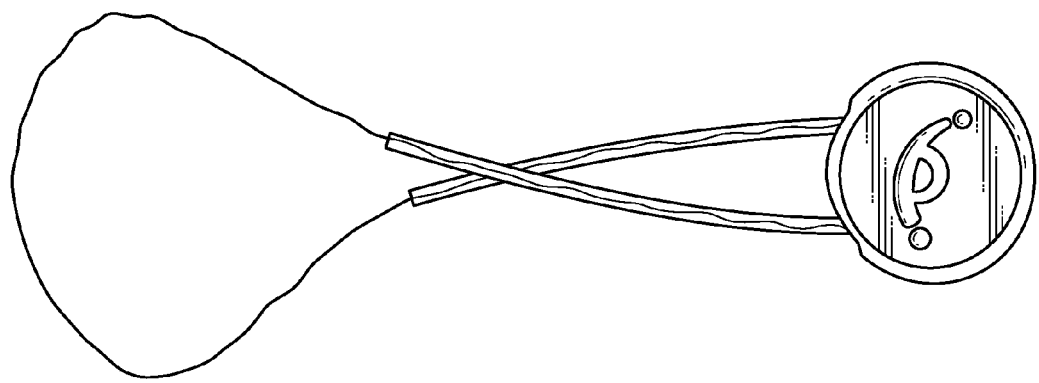
FIG. 3 shows a photograph of newly developed disposable electrodes in the form of loops with counterweights.

For hygienic reasons, the electrodes were EO (ethylene oxide) sterilized and delivered in the form of a loop. A small button-shaped counterweight ensures a certain amount of mechanical tension while also giving the patient a means of grasping and holding them; see FIG. 3.

Positioning on the Eye

In order to position the thread electrode on the eye in spite of the patient's visual handicap, it is necessary to establish reproducible points of reference at which the electrode can be attached to the head and remain in contact with the edge of the lid at the assigned position. Two different approaches for creating these points of reference are disclosed in above mentioned WO 2011/086150 A2.

a) Face Mask

A mask is fitted to the patient's facial eye area, much like a plaster cast for fractures. Plastic sheets cut to size are heat-softened in warm water, then pressed gently into place around the facial eye area. The material remains pliable for about ½ hour and can be molded to the facial contours during that time. Subsequently, smaller adjustments are possible by means of a jet of hot air for renewed, local warming.

The facial area around the eyes is then cut away with scissors, and buttons which will later hold the electrodes are pressed into the mask at its corners.

These buttons are pre-assembled with connection wires for the electric current supply or for connection to a standard commercial skin electrode which serves as a counter-electrode. The intention is for the patient simply to connect a thread electrode (with matching buttons on its ends) by pressing it into place; after a bit of practice, this can easily be accomplished by searching and feeling with the fingers.

After the facial mask has been correctly fitted, the thread electrode is allowed to fall onto the corneal surface of the open eye, where it is barely felt. It is recommended that the patients keep their eyes closed after emplacement of the electrodes in order to avoid excessive mechanical irritation of the cornea and prevent the thread electrode from slipping out of place.

The use of plaster casts is standard practice in many orthopedic centers and hospitals, for example as a means of stabilizing bone fractures. The manual techniques for fitting masks as described above are thus already available.

b) Lens Frame

The technique of pinpointing positions on the face with the help of a lens frame has been known for centuries and has proven reliable. It is already known from the field of optometry that spectacles can be adjusted in this way with an accuracy of about 1 mm, which is extremely important for progressive lenses in particular.

Figure 4:
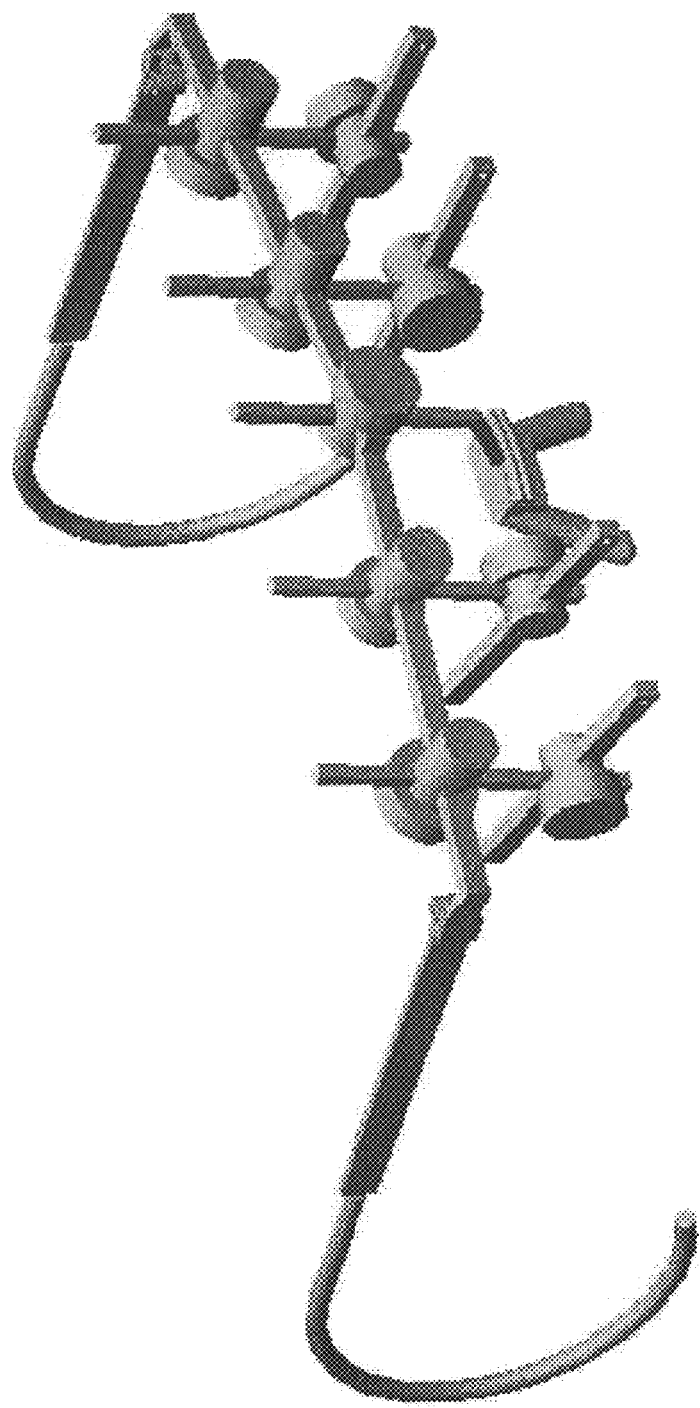
FIG. 4 shows a sketch of a device for positioning thread electrodes on the eyes.

This alternative approach therefore uses the same type of lens frames as those used by competitive marksmen to support a retractable occluder or aperture. In the present case, two adjustable pins were attached to this frame for each eye; these were horizontally and vertically adjustable in such a way that they nearly touched the corners of the eyelids; see FIG. 4. This initially required a bit of manual dexterity at the beginning, but no special expertise.

The pins are electrically conductive and have notches facing the eye; in each case, the loop-shaped, thread electrodes are positioned in these notches. The button-shaped counterweight puts light tension on the thread, holding it against the corneal surface. The pins are connected by a wire to the electric power supply, and another wire conductor attached to the lens frame leads to a standard commercial skin electrode, also with a button, which serves as counter-electrode.

This skin electrode is kept in position around the temple of the head by an electrically conducting gel.

The Control Unit

The electronic control unit must be capable of meeting demands which initially appear mutually exclusive. On the one hand, it should allow the attending physician to specify the individual phosphene threshold, thus offering a flexible array of settings. On the other, it should provide the patient with a treatment designed for him/her alone, without optional settings, and without requiring residual vision for its use.

Initial observations made it clear that the idea of two different devices, one for the physician and one for the patient, was too complicated, and that it would be simpler to use a single device which the physician could connect by USB to his PC; he could then vary the stimulation current by means of a graphic user interface.

As it turned out, the electronic control unit requires less than 1 minute in standard threshold mode to increase stimulation current in 60 logarithmic steps from 5 µA to 10 mA. When the patient reports seeing the first phosphene, which typically occurs at about 1 mA, the physician stops the process. He can then determine the desired individual treatment parameters (pulse form, strength of current, duration of treatment) and store them on a miniature USB flash memory stick.

These data are stored in encrypted form so that the above-mentioned treatment parameters can be changed only with the physician's own software. The electronic control unit also has a connection designed specifically for this memory stick format so that other standard commercial USB sticks cannot be inserted into it.

Typical pulse data (30 minutes a week) are: biphasic, stimulus currents of 5 ms duration for each positive and negative pulse, and a repetition rate of 20 Hz.

The physician can now leave the device (with the memory stick) in the patient's possession for use at home or, if the patient already has such a device, simply give the patient the memory stick. The treatment parameters actually used by the patient (pulse data, current strength, time and duration of treatment) are then stored on the memory stick; the physician can check the patient's compliance at their next meeting, and can also store and process the data himself.

Figure 5:
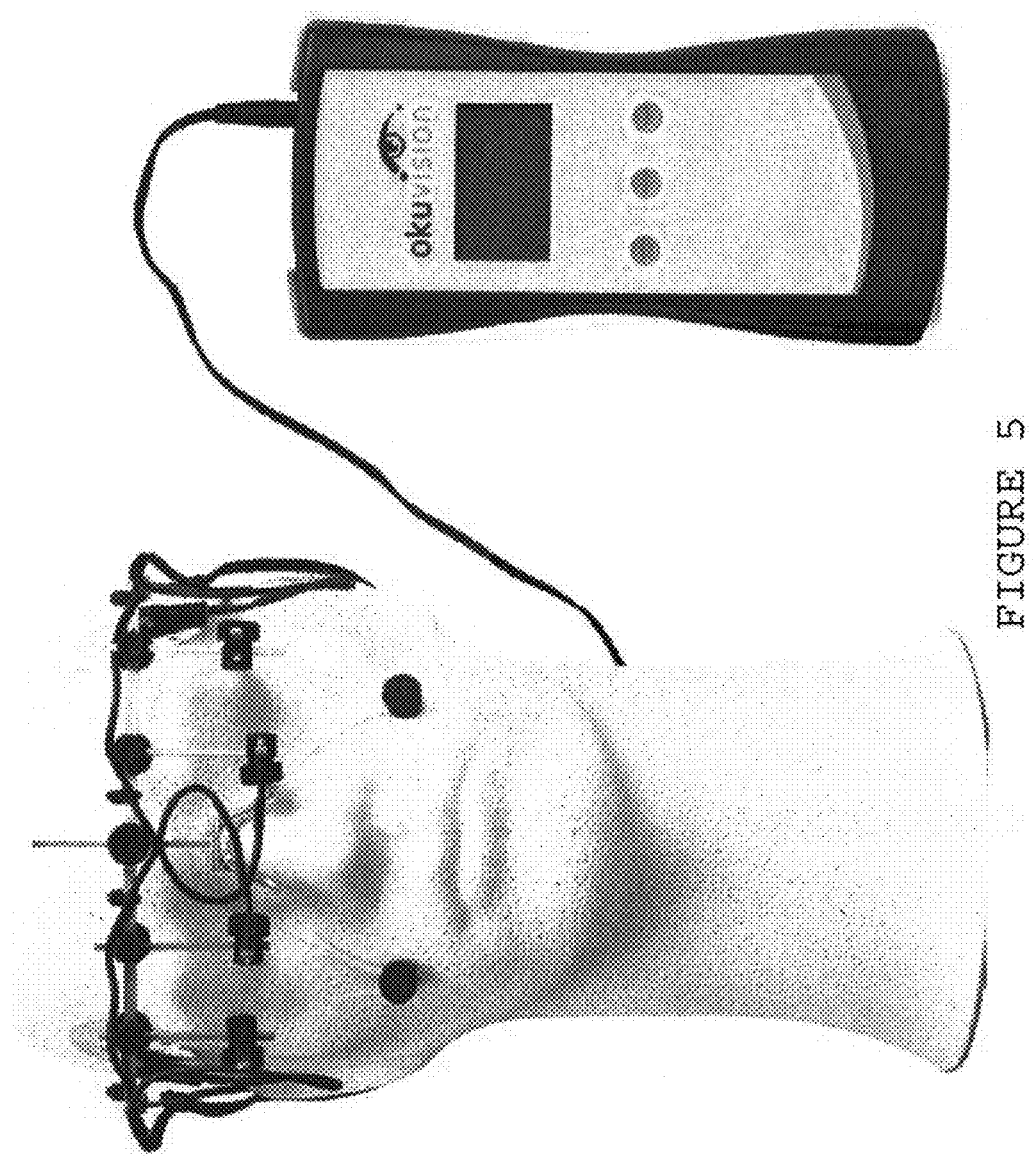
FIG. 5 shows the new treatment system comprising disposable electrode, with positioning device and an electronic control unit.

The device itself is battery-powered and transportable (weight: 430 g). A set of standard commercial batteries lasts for several weeks of stimulation in normal use. The patient's foil-type keypad is designed with only three buttons for tactile recognition: ON/OFF/STOP, PAUSE, and START; see FIG. 5. Constant pressure on ON/OFF/STOP turns the device on and off. Pressing it briefly interrupts stimulation; this is recorded in the protocol. The PAUSE button, in turn, interrupts stimulation only temporarily.

Acoustic signals inform the patient of the status of the device at all times. A rhythmic tone with gradually increasing speed means that the device has just been turned on, a rhythmic, gradually slower tone means that it has just been turned off. Correct stimulation is indicated by a tone which sounds like the ticking of a clock (with a soothing effect).

If the thread-like electrode wire is not correctly positioned on the eye or if a short circuit occurs, this is indicated by corresponding, intensive warning tones (or, if a PC is used as control device, only by an icon on the monitor screen). For this purpose the device has a compliance detector which constantly compares current delivered with the actual electric potential in order to determine the impedance of the patient/electrode system which is connected.

200 Ohm and 5 kOhm were empirically determined as limit values. A value of less than 200 Ohm can occur only if the electrodes are connected in such a way that a short circuit occurs. Values of more than 5 kOhm mean that the thread electrode wire is not well positioned on the eye but rather—for example—on the outer eyelid or that no thread electrode is present at all.

The detector thus also gives a warning if the skin electrode is positioned—contrary to instructions—without prior removal of fat from the skin area. This detector has proven to be very helpful, since the correct position of the thread on the cornea cannot be reliably perceived by the sense of touch alone when the lens frame with its electrode is put on, and can be ascertained even by persons with normal vision only under optimum lighting. The actual treatment times are also recorded on the flash memory stick and provide information to the physician who reviews the protocol as to whether and to what extent the patient has successfully coped with the system.

An LCD display shows patient impedance at every moment and notifies of any errors which may occur. However, such information is relevant only in case of problems with the device and is therefore intended only for the physician or persons caring for the patient.

Final Remarks

The system described here makes electrical stimulation available for treatment based on clinical data gathered by a universally respected German university hospital in accordance with Good Clinical Practice. The treatment parameters will require further testing and optimization in further, more comprehensive clinical studies. With a bit of practice, the new stimulation system can be used under the direction of a physician by both medical staff assistants and by the patients themselves. The system also helps lay the groundwork for carrying out multicentered studies in this medical area. Initial reactions from patients indicate major interest.

As used herein, "a" or "an" means "at lest one" or "one or more".

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in the present application is contrary to or otherwise inconsistent with a definition set forth in the patents, applications, published applications and other publications that are herein incorporated by reference, the definition set forth in the present application prevails over the definition that is incorporated herein by reference.

Therefore, what is claimed, is:

1. A method for treating at least one eye of a patient in need of such treatment, comprising the step of applying a pulsed electrical stimulation signal to the at least one eye,
   wherein at least one stimulation parameter of the pulsed electrical stimulation signal is set depending on at least one individual parameter of the patient,
   wherein the at least one individual parameter of the patient is a base line stimulation current that results in the perception of electrically triggered light phenomena in the at least one eye of the patient,
   wherein the at least one eye is stimulated with a stimulation current that is higher than the base line stimulation current,
   wherein the at least one stimulation parameter is a stimulation current flowing via the cornea into the at least one eye, and
   wherein the base line stimulation current is determined individually for each patient by:
      applying to the at least one eye a pulsed electrical stimulation signal which has initially a stimulation current low enough as to not elicit a phosphene,
      increasing the stimulation current until the patient reports the perception of a phosphene,
      taking the corresponding stimulation current as the base line stimulation current, and
      setting the at least one stimulation parameter depending on the base line stimulation current.

2. The method of claim 1, wherein the stimulation current is at least 110% of the base line stimulation current.

3. The method of claim 2, wherein the stimulation current is between 110% and 200% of the base line stimulation current.

4. The method of claim 3, wherein the stimulation current is between 140% and 160% of the base line stimulation current.

5. The method of claim 1, wherein the pulsed electrical stimulation signal comprises a succession of current pulses and has a stimulation duration time, a pulse duration time and a pulse repetition frequency.

6. The method of claim 1, wherein the treatment is repeated at least once per week, month or year.

7. The method of claim 1, further comprising the step of attaching a thread electrode to the at least one eye, such that it makes direct or indirect electrical contact to the cornea, and a counter electrode to a skin portion of the patient, the thread electrode and the counter electrode being part of an electrical circuit for applying the pulsed electric stimulation signal to the at least one eye.

8. The method of claim 7, wherein the counter electrode is attached to the temple.

9. The method of claim 7, wherein the thread electrode is positioned in the conjunctival sac.

10. The method of claim 7, wherein the thread electrode is positioned on the edge of the lid of the at least one eye.

11. The method of claim 1, wherein the base line stimulation current is determined at least three times in succession and the arithmetic mean value of said three base line stimulation currents is calculated and used as the base line stimulation current for subsequent treatments of the at least one eye.

12. The method of claim 1, wherein the pulsed electric stimulation signal is generated by a control unit which has stored therein variable parameters for said pulsed electric stimulation signal, said parameters comprising at least a value representing the stimulation current.

13. The method of claim 12, wherein the stimulation current value is determined by a qualified person different from the patient, and stored into the control unit such that it can be altered only by the or another qualified person.

14. The method of claim 12, wherein the stimulation current value is stored on a data memory that can be put into communication with the control unit.

15. The method of claim 1, wherein the pulsed electrical stimulation signal comprises a stimulation duration time of about 30 min each week, a succession of biphasic voltage pulses having each a pulse duration time of about 5 ms and a pulse repetition frequency of about 20Hz.

16. The method of claim 1, wherein the patient feels the need for the treatment, or suffers from retinitis pigmentosa, macular detachment, glaucoma, macular degeneration, retinal detachment, retinal artery occlusion, retinal vein occlusion, non-arteriitic anterior ischemic optic neuropathy, or ischemic macula edema.

17. A method for treating at least one eye of a patient in need of such treatment with a pulsed electrical stimulation signal, comprising:
  determining a base line stimulation current that results in the perception of electrically triggered light phenomena in at least one eye of a patient;
  setting a pulsed electrical stimulation signal having a stimulation current higher than the base line stimulation current determined individually of the at least one eye of the patient;
  applying the pulsed electrical stimulation signal to the at least one eye,
  wherein the pulsed electrical stimulation signal is applied to the at least one eye via the cornea of the at least one eye, and
  wherein the base line stimulation current corresponds to an individual phosphene threshold of the at least one eye of the patient.

18. The method of claim 17, wherein the stimulation current is at least 110%, between 110% and 200%, or between 140% and 160% of the base line stimulation current.

19. The method of claim 17, further comprising the step of attaching a thread electrode to the at least one eye, such that it makes direct or indirect electrical contact to the cornea, and a counter electrode to a skin portion of the patient, the thread electrode and the counter electrode being part of an electrical circuit for applying the pulsed electric stimulation signal to the at least one eye.

20. The method of claim 19, wherein the counter electrode is attached to the temple.

21. The method of claim 19, wherein the thread electrode is positioned in the conjunctival sac or on the edge of the lid of the at least one eye.

22. The method of claim 17, wherein the patient feels the need for the treatment, or suffers from retinitis pigmentosa, macular detachment, glaucoma, macular degeneration, retinal detachment, retinal artery occlusion, retinal vein occlusion, non-arteriitic anterior ischemic optic neuropathy, or ischemic macula edema.

23. A method for treating at least one eye of a patient in need of such treatment, comprising the step of applying one pulsed electrical stimulation signal to the at least one eye,
  wherein at least one stimulation parameter of the pulsed electrical stimulation signal is set depending on at least one individual parameter of the patient,
  wherein the at least one individual parameter of the patient is a base line stimulation current that results in the perception of electrically triggered light phenomena in the at least one eye of the patient,
  wherein the at least one eye is stimulated with a stimulation current that is higher than the base line stimulation current,
  wherein the at least one stimulation parameter is a stimulation current flowing via the cornea into the at least one eye, and
  wherein the base line stimulation current is determined individually for each patient by:
    applying to the at least one eye one pulsed electrical stimulation signal which has initially a stimulation current low enough as to not elicit a phosphene,
    increasing the stimulation current until the patient reports the perception of a phosphene,
    taking the corresponding stimulation current as the base line stimulation current, and
    setting the at least one stimulation parameter depending on the base line stimulation current.

* * * * *